United States Patent [19]
Philippe et al.

[11] Patent Number: 5,948,415
[45] Date of Patent: *Sep. 7, 1999

[54] ORNITHINE DERIVATIVES, A PROCESS FOR THEIR PREPARATION, METHODS OF THEIR USE AND A COMPOSITION COMPRISING THEM

[75] Inventors: Michel Philippe, Wissous; Thierry Bordier, Tremblay en France, both of France

[73] Assignee: L'Oreal, Paris, France

[*] Notice: This patent is subject to a terminal disclaimer.

[21] Appl. No.: 08/633,497

[22] Filed: Apr. 17, 1996

[30] Foreign Application Priority Data

Apr. 20, 1995 [FR] France ................... 95 04746

[51] Int. Cl.$^6$ ............... A61K 6/00; A61K 7/00; C07C 261/00; C07C 229/00

[52] U.S. Cl. ............ 424/401; 424/450; 424/489; 424/59; 424/63; 424/64; 424/78.02; 424/43; 424/49; 424/70.7; 424/70.31; 560/156; 560/169; 562/561; 562/562

[58] Field of Search ............... 424/401, 70.31, 424/489, 402, 487, DIG. 65, 450, 59, 63, 64, 78.02, 43, 49, 70.7; 435/182, 177; 514/476, 478, 944, 562, 844, 937, 945; 560/156, 169; 562/561, 562

[56] References Cited

U.S. PATENT DOCUMENTS

| | | |
|---|---|---|
| 5,206,012 | 4/1993 | Farer et al. . |
| 5,216,023 | 6/1993 | Literati Nagi et al. .................. 514/538 |
| 5,230,890 | 7/1993 | Philippe et al. . |
| 5,412,125 | 5/1995 | Philippe ..................... 554/35 |
| 5,529,914 | 6/1996 | Hubbell et al. .......................... 435/182 |
| 5,587,169 | 12/1996 | Philippe et al. ......................... 424/401 |
| 5,593,680 | 1/1997 | Bara et al. .............................. 424/401 |
| 5,686,085 | 11/1997 | Bordier et al. .......................... 424/401 |
| 5,688,527 | 11/1997 | Bordier et al. .......................... 424/450 |

FOREIGN PATENT DOCUMENTS

| | | |
|---|---|---|
| A-0139481 | 5/1985 | European Pat. Off. . |
| A-0336265 | 10/1989 | European Pat. Off. . |
| A-0408448 | 1/1991 | European Pat. Off. . |
| A-0447287 | 9/1991 | European Pat. Off. . |
| A-0545786 | 6/1993 | European Pat. Off. . |

OTHER PUBLICATIONS

Derwent Abstract of EP–A–0545786.

*Primary Examiner*—Lynette F. Smith
*Assistant Examiner*—Datquan Lee
*Attorney, Agent, or Firm*—Finnegan, Henderson, Farabow, Garrett & Dunner, L.L.P.

[57] ABSTRACT

The present invention relates to new compounds, which are $N^\delta$-substituted ornithine derivatives, having the formula (I)

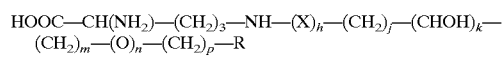

in which R represents a hydrocarbon alkyl radical or a perfluorinated alkyl radical, X is a divalent radical chosen from —CO—O—, —CO—NH— and —SO$_2$—, h, j, k, m and n are, independently, zero or 1 and p is zero to 4, a salt of a compound of formula (I), an optical isomer of D or L configuration thereof or a mixture thereof. The invention also relates to a process for the preparation of these compounds, to their use, especially in cosmetics, and to compositions, especially cosmetic compositions, comprising them.

19 Claims, No Drawings

ORNITHINE DERIVATIVES, A PROCESS FOR THEIR PREPARATION, METHODS OF THEIR USE AND A COMPOSITION COMPRISING THEM

The present invention is directed to compounds, which are derived from ornithine, a process for their preparation, methods for their use, especially in cosmetics, and to compositions, especially cosmetic compositions, comprising them.

Compositions, especially cosmetic, pharmaceutical and food compositions, are known which can be provided in the form of a powder, known as a compact powder. These are generally anhydrous compositions which may be mainly composed of solid particles and of a fatty binder, shaped by compression. The development of such compositions raises, however, many difficulties because the final composition must be sufficiently homogeneous and compact to have a good ability to be removed and, moreover, to avoid fragmentation which may be caused, especially, by impact.

A description is given, in European Patent Application EP 139,481, of cosmetic compositions using, as agents for modifying the surface of inorganic compounds, for the purpose of increasing the dispersibility thereof, either a monoacylated derivative of a basic amino acid in which the aliphatic acyl group has 8–22 carbon atoms or an N,N-diacylated derivative of a basic amino acid in which the acyl groups, which are identical or different, have 1–22 carbon atoms.

A description is also given, in European Patent Application EP 336,265, of cosmetic compositions for hair shaping comprising, as surface-active agents, an N-monoacylated derivative of a basic amino acid in which the acyl group has 8–22 carbon atoms.

However, it is observed that the acylated derivatives of the basic amino acids described previously can be very difficult and even impossible to compact.

The aim of the present invention is to provide new compounds which make it possible to facilitate the preparation of such compositions, while satisfying the above-mentioned requirements, without exhibiting the disadvantages of the prior art.

A first subject of the present invention is therefore a compound of formula (I):

HOOC—CH(NH$_2$)—(CH$_2$)$_3$—NH—(X)$_h$—(CH$_2$)$_j$—(CHOH)$_k$—(CH$_2$)$_m$—(O)$_n$—(CH$_2$)$_p$—R in which
  R represents a saturated or unsaturated, linear or branched, hydrocarbon alkyl radical having from 8 to 30 carbon atoms or a saturated or unsaturated, linear or branched, perfluorinated alkyl radical having from 4 to 20 carbon atoms,
  X is a divalent radical chosen from —CO—O—, —CO—NH— and —SO$_2$—,
  h, j, k, m and n independently represent zero or 1, and
  p is equal to zero to 4,
a salt of the compound of formula (I), an optical isomer of D or L configuration with respect to the chiral center

HOOC—CH.(NH$_2$)— of a compound of formula (I) and their mixtures.

Another subject of the invention is a composition, including a cosmetic, pharmaceutical, hygiene or food composition, comprising at least one compound of formula (I), salt or optical isomer thereof.

It has in fact been observed that the compounds according to the invention made it possible to confer particularly advantageous spreading and skin-adhesion qualities, as well as a pleasant and smooth feel and an improved water-resistance, to the cosmetic composition comprising them.

A further subject of the invention is a method for coating substrate particles, which comprises applying a composition comprising at least one compound of formula (I), salt or optical isomer thereof to at least one substrate particle in an amount effective to at least partially coat the at least one substrate particle.

It has in fact been observed that the substrate particles, generally powders, had an improved feel when they were coated, at least partially, with at least one compound, salt or optical isomer according to the invention.

Another subject of the invention is a method for improving the compacting of a powder composition, which comprises including in the powder composition at least one compound of formula (I), salt or optical isomer thereof in an amount effective to improve the compacting of the powder composition.

The above-mentioned first subject of the invention is therefore at least one compound of formula (I):

HOOC—CH(NH$_2$)—(CH$_2$)$_3$—NH—(X)$_h$—(CH$_2$)$_j$—(CHOH)$_k$—(CH$_2$)$_m$—(O)$_n$—(CH$_2$)$_p$—R salt or optical isomer thereof.

Mention may preferably be made, among the compounds according to the invention, of N$^\delta$-dodecyloxycarbonyl-L-ornithine, N$^\delta$-dodecylsulphonyl-L-ornithine and N$^\delta$-dodecylaminocarbonyl-L-ornithine.

The salts of the compounds according to the invention can be chosen from the salts of monovalent inorganic cations, such as those of sodium, or divalent inorganic cations, such as those of zinc or of copper. The salts can also be chosen from the salts of organic cations, such as those of aminopropanediol, trishydroxyaminomethane, glucamine and N-methylglucamine.

The compounds according to the invention can be provided in solid particle form having a particle size generally ranging from 10 to 500,000 nm and preferably from 100 to 25,000 nm.

The compounds according to the invention are generally insoluble in oils and in aqueous solutions in which the pH ranges from 5 to 8.

The composition according to the invention comprising the compounds can be provided in various forms such as dispersions, optionally thickened or gelled lotions, optionally compacted powders, milks, creams, sticks, foams or sprays when it is packaged as an aerosol, oil-in-water, water-in-oil or multiple emulsions, liposomal dispersions or alternatively solid preparations.

The compounds according to the invention can be included in the composition according to the invention in a proportion preferably ranging from 0.05% to 80% by weight, and more preferably in a proportion from 0.5 to 30% by weight, with respect to the total weight of the composition.

The compounds according to the invention can be present in the composition according to the invention in free form and/or in the form of a combination with at least one substrate particle wherein the at least one substrate particle is at least partially coated, preferably with the at least one compound, salt or optical isomer of the present invention.

In addition to the compound according to the invention, the composition according to the invention can also comprise at least one additive chosen from the group comprising surface-active agents, fatty substances, organic solvents, silicones, thickeners, emollients, sunscreen agents, treating agents, anti-foaming agents, moisturizing agents, fragrances, preservatives, antioxidizing agents, sequestrants, flavoring agents, basifying or acidifying agents, fillers and pigments. Mention may preferably be made, among the fatty substances which can be used in the composition according to the invention, of oils, waxes, fatty acids, fatty alcohols and a mixture of these substances.

The oils can be of animal, plant, inorganic or synthetic origin. Mention may preferably be made of hydrogenated palm oil, hydrogenated castor oil, liquid petrolatum, liquid paraffin and purcellin oil.

The waxes can also be of animal, plant, mineral or synthetic origin. Mention may preferably be made of beeswax, montan wax, carnauba wax, candelilla wax, sugar cane wax, Japan wax, ozocerite, microcrystalline waxes, paraffin wax, lanolin wax, hydrogenated lanolin wax and acetylated lanolin wax.

Mention may preferably be made, among the substrate particles which can be coated, partially or completely, by the at least one compound, salt or optical isomer according to the invention, of pigments, particulate fillers and microspheres such as hollow vinylidene chloride/acrylonitrile copolymer microspheres. Mention may more preferably be made, among the fillers, of optionally colored insoluble fillers such as nanopigments of metal oxides, such as titanium, zinc, iron, manganese, caesium and zirconium oxides.

The composition according to the invention can thus find an application as a make-up composition such as a foundation cream, a tinted cream, a mascara, a blusher, an eye shadow, a lipstick or a nail varnish. According to a preferred embodiment, the composition of the invention can be provided in a so-called compact form, the compound according to the invention facilitating the compacting of the ingredients of the compositions.

Mention may preferably be made, among these compact compositions, of foundation creams, blushers, eye shadows and lipsticks.

The composition according to the invention can also be provided in the form of a pharmaceutical or hygiene composition, such as a toothpaste, an exfoliative composition, a powder for the body or for babies, and an antiperspirant powder, or also in the form of a food composition.

Another subject of the invention is a process for the preparation of an ornithine derivative compound of formula (I), salt or optical isomer thereof, which process comprises the steps of:

(a) reacting, in aqueous medium and at basic pH, ornithine or a salt of ornithine of known configuration, with a solution of a copper salt to form a copper complex, (b) reacting the solution of the copper complex with a compound of formula (II) chosen from:
(IIa) $R'—CO—O—(CH_2)_j—(CHOH)_k—(CH_2)_m—(O)_n—(CH_2)_p—R$,
(IIb) $O=C=N—(CH_2)_j—(CHOH)_k—(CH_2)_m—(O)_n—(CH_2)_p—R$,
(IIc) $R''—CO—NH—(CH_2)_j—(CHOH)_k—(CH_2)_m—(O)_n—(CH_2)_p—R$,
(IId) $Cl—SO_2—(CH_2)_j—(CHOH)_k—(CH_2)_m—(O)_n—(CH_2)_p—R$, and

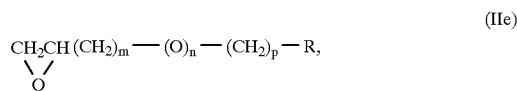

in which R is as defined above, R' represents a chlorine atom, a chloromethyl radical or an azolyl radical and R" represents an azolyl radical, (c) treating the copper salt of the substituted ornithine compound obtained from step (b) with a decomplexing agent and, optionally, (d) purifying the compound obtained from step (c).

Mention may preferably be made, among the copper salt solutions which can be used in the process according to the invention, of copper sulphate solutions.

The basic pH of the reaction medium preferably ranges from 8 to 14.

The azolyl radical is preferably an imidazolyl radical. The compound of formula (II) can be added with or without solvent.

The decomplexing agent used is preferably an aqueous solution of the disodium salt of EDTA acid or of an acid such as hydrochloric acid.

Examples of the preparation of compounds according to the invention are given below, as well as an example of a composition comprising such a compound.

EXAMPLE 1

Preparation of $N^\delta$-dodecyloxycarbonyl-L-ornithine $R=C_{12}H_{25}$, $X=$—COO—, $h=1$, $j=k=m=n=p=0$ 5 g of L-ornithine monohydrochloride were dissolved in 24 ml of a 10% aqueous sodium hydroxide solution in a 100 ml round-bottomed flask. A solution of 3.7 g of copper sulphate pentahydrate in 40 ml of water was added. 2.49 g of sodium hydrogencarbonate, followed by 1 eq. of dodecyl chloroformate in solution in THF, were added to the reaction mixture, which had been cooled to 5° C.

After stirring for 16 hours at room temperature, the reaction medium was filtered and the precipitate was washed and dried under reduced pressure. The complex was treated at reflux for 2 h with a 10% aqueous solution of the dihydrated disodium salt of EDTA acid.

7.4 g (73% yield) of white product were obtained.
Chemical analysis gave the following characteristics:
Melting: T>260° C.
Mass spectrum: m/z 345.2 ($MH^+$), 299.2, 282.2
Elemental analysis: ($C_{18}H_{36}N_2O_4$, molecular weight 344.499)

|  | C | H | F | N |
|---|---|---|---|---|
| % calculated | 62.76 | 10.53 | 8.13 | 18.58 |
| % measured | 62.61 | 10.60 | 8.37 | 18.52 |

Particle size (Coulter Counter TA2): number (-average): 3.15 μm

Thin layer chromatography: HPTLC (Merck silica 60F254), with, as eluent, a 6/47/47 $NH_4OH/CH_3OH/CH_2Cl_2$ mixture.

A frontal ratio $R_f=0.59$ was obtained.

EXAMPLE 2

Preparation of $N^\delta$-dodecylsulphonyl-L-ornithine $R=C_{12}H_{25}$, $X=$—$SO_2$—, $h=1$, $j=k=m=n=p=0$ 5 g of L-ornithine monohydrochloride were dissolved in 24 ml of a 10% aqueous sodium hydroxide solution in a 100 ml round-bottomed flask. A solution of 3.7 g of copper sulphate pentahydrate in 40 ml of water was added. 2.49 g of sodium hydrogencarbonate, followed by 1 eq. of dodecanesulphonyl chloride in solution in THF, were added to the reaction mixture, which had been cooled to 5° C. After stirring for 16 hours at room temperature, the reaction medium was filtered and the precipitate was washed and dried under reduced pressure. The complex was treated at reflux for 2 h with a 10% aqueous solution of the dihydrated disodium salt of EDTA acid.

3.9 g (36% yield) of white product were obtained.

Chemical analysis gave the following characteristics:

Melting: T>260° C.

Mass spectrum: m/z 365 (MH$^+$), 347.2, 302.2

Elemental analysis: ($C_{17}H_{36}N_2O_4S$, molecular weight 364.551)

|            | C     | H     | N    | O     | S    |
|------------|-------|-------|------|-------|------|
| % calculated | 56.01 | 9.95  | 7.68 | 17.56 | 8.80 |
| % measured   | 56.07 | 10.16 | 7.76 | 17.64 | 8.93 |

Particle size (Coulter Counter TA2): number (-average): 2.19 μm

Thin layer chromatography: HPTLC (Merck silica 60F254), with, as eluent, a 6/47/47 $NH_4OH/CH_3OH/CH_2Cl_2$ mixture.

A frontal ratio $R_f$=0.48 was obtained.

EXAMPLE 3

Preparation of a compacted powder

A powder was prepared which had the following composition:

| Talc                | 38.4 g |
|---------------------|--------|
| Bismuth oxychloride | 10 g   |
| Zinc stearate       | 4 g    |
| Compound of Example 1 | 20 g |
| Nylon powder        | 20 g   |
| Iron oxides         | 1.6 g  |
| Liquid petrolatum   | 6 g    |

The powder was obtained in the following way: the constituents, except for the liquid petrolatum, were ground in a grinder of Kenwood type for approximately 5 minutes with slow agitation. The liquid petrolatum was added, and the entire mixture was ground for approximately 2 minutes at the same speed and then for 3 minutes at a faster speed. The preparation was then sieved on a 0.16 mm sieve, and this mixture was then compacted into small dishes (40 bar).

A compacted powder was obtained which had good adhesion and which spread readily and pleasantly on the skin, while being smooth to the touch.

EXAMPLE 4

Preparation of a compacted powder

A powder was prepared which had the following composition:

| Talc                | 38.4 g |
|---------------------|--------|
| Bismuth oxychloride | 10 g   |
| Zinc stearate       | 4 g    |
| Compound of Example 2 | 20 g |
| Nylon powder        | 20 g   |
| Iron oxides         | 1.6 g  |
| Liquid petrolatum   | 6 g    |

The powder was obtained in a way similar to Example 3.

A compacted powder was obtained which had good adhesion and which spread readily and pleasantly on the skin, while being smooth to the touch.

EXAMPLE 5

The compositions of Examples 3 and 4 were compared with:

(I) The same composition in which the compounds of the invention were completely replaced by mica (control composition I) and (II) the same composition in which the compounds of the invention were completely replaced by Amihope sold by Ajinomoto (control composition II).

A drop test was then carried out which consisted of allowing the compacts obtained to fall, twice, from a height of 1 m and then weighing them, so as to determine the % of powder removed.

The following results were obtained:

|                    | Control I         | Control II              | Example 3                 | Example 4                    |
|--------------------|-------------------|-------------------------|---------------------------|------------------------------|
| Loss (% by weight) | 3%                | 1%                      | 0.5%                      | 0%                           |
| Comments           | much disintegration | moderate disintegration | moderate/low disintegration | virtually no disintegration |

It was thus noted that the control compositions disintegrated much more easily than the compositions according to the invention.

The presence of the compounds according to the invention made it possible to markedly improve the cohesion of the compacted product.

What is claimed is:

1. An ornithine derivative compound of formula (I):

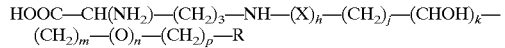

in which

R represents a saturated or unsaturated, linear or branched, hydrocarbon alkyl radical having from 8 to 30 carbon atoms or a saturated or unsaturated, linear or branched, perfluorinated alkyl radical having from 4 to 20 carbon atoms, X is a divalent radical selected from —CO—O—, —CO—NH— and —SO$_2$—, h, j, k, m and n independently represent zero or 1, and p is equal to zero to 4;

a salt of a compound of formula (I), an optical isomer of D or L configuration with respect to the chiral center

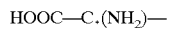

of a compound of formula (I), or a mixture of any of these compounds.

2. A compound according to claim 1, wherein said salt is selected from the salts of monovalent or dilavent inorganic cations and the salts of organic cations.

3. A compound according to claim 1, which is $N^\delta$-dodecyloxycarbonyl-L-ornithine, $N^{67}$-dodecylsulphonyl-L-ornithine or $N^\delta$-dodecylaminocarbonyl-L-ornithine.

4. A compound according to claim 1, said compound being present in the form of particles having a particle size ranging from 10 nm to 500,000 nm.

5. A composition which comprises at least one ornithine derivative compound of formula (I) or salt thereof or optical isomer thereof according to claim 1.

6. A composition according to claim 5, wherein said at least one compound of formula (I), salt, or optical isomer is present in an amount ranging from 0.05 to 80% by weight with respect to the total weight of the composition.

7. A composition according to claim 6, wherein said at least one compound of formula (I), salt, or optical isomer is present in an amount ranging from 0.5 to 30% by weight with respect to the total weight of the composition.

8. A composition according to claim 5, wherein said at least one compound of formula (I), salt, or optical isomer is present in free form or in the form of a combination with at least one substrate particle, and further wherein said at least one compound, salt, or optical isomer of formula (I) at least partially coats said at least one substrate particle.

9. A composition according to claim 8, wherein said at least one substrate particle is selected from pigments, particulate fillers and microspheres.

10. A composition according to claim 5, which is the form of a cosmetic, pharmaceutical, hygiene or food composition.

11. A composition according to claim 5, which is in the form of a dispersion, an optionally thickened or gelled lotion, an optionally compacted powder, a milk, a cream, a stick, a foam, a spray, an emulsion, a liposomal dispersion or a solid preparation.

12. A composition according to claim 10, wherein said cosmetic composition is in the form of a make-up composition.

13. A process for the preparation of an ornithine derivative compound of formula (I), salt, or optical isomer according to claim 1, which comprises the steps of:
(a) reacting, in aqueous medium and at basic pH, ornithine or a salt of ornithine of known configuration, with a solution of a copper salt to form a copper complex;
(b) reacting the solution of said copper complex with a compound of formula (II) selected from:
(IIa) $R'\!-\!CO\!-\!O\!-\!(CH_2)_j\!-\!(CHOH)_k\!-\!(CH_2)_m\!-\!(O)_n\!-\!(CH_2)_p\!-\!R$,
(IIb) $O\!=\!C\!=\!N\!-\!(CH_2)_j\!-\!(CHOH)_k\!-\!(CH_2)_m\!-\!(O)_n\!-\!(CH_2)_p\!-\!R$,
(IIc) $R''\!-\!CO\!-\!NH\!-\!(CH_2)_j\!-\!(CHOH)_k\!-\!(CH_2)_m\!-\!(O)_n\!-\!(CH_2)_p\!-\!R$,
(IId) $Cl\!-\!SO_2\!-\!(CH_2)_j\!-\!(CHOH)_k\!-\!(CH_2)_m\!-\!(O)_n\!-\!(CH_2)_p\!-\!R$, and $$\text{(IIe)} \quad \underset{O}{CH_2\!-\!CH}\!-\!(CH_2)_m\!-\!(O)_n\!-\!(CH_2)_p\!-\!R,$$

in which R is as defined in claim 1, R' represents a chlorine atom, a chloromethyl radical or an azolyl radical and R" represents an azolyl radical; and (c) treating the copper salt of the substituted ornithine compound obtained from step (b) with a decomplexing agent.

14. A method for coating a substrate particle, which comprises applying a composition comprising at least one ornithine derivative compound, salt, or optical isomer according to claim 1 to a substrate particle in an amount effective to at least partially coat said substrate particle.

15. A method for improving the compacting of a powder composition, which comprises including in a powder composition to be compacted at least one ornithine derivative compound, salt, or optical isomer according to claim 1 in an amount effective to improve the compacting of said powder composition.

16. A composition according to claim 9, wherein said microspheres are hollow vinylidine chloride/acrylonitrile copolymer microspheres.

17. A composition according to claim 12, wherein said makeup composition is a foundation cream, a tinted cream, a mascara, a blusher, an eye shadow, a lipstick or a nail polish.

18. A composition according to claim 5, wherein said hygiene composition is an exfoliative composition, a toothpaste, a powder for the body, a powder for babies or an anti-perspirant powder.

19. A process according to claim 13, wherein following said treating, the compound obtained from step (c) is purified.

* * * * *

UNITED STATES PATENT AND TRADEMARK OFFICE
CERTIFICATE OF CORRECTION

PATENT NO. : 5,948,415
DATED : September 7, 1999
INVENTOR(S) : Michel Philippe et al.

It is certified that error appears in the above-identified patent and that said Letters Patent is hereby corrected as shown below:

<u>IN THE CLAIMS</u>:

Claim 3, col. 7, line 2, "$N^{67}$" should read --$N^6$--.

Signed and Sealed this

Twenty-ninth Day of February, 2000

Attest:

Q. TODD DICKINSON

Attesting Officer

Commissioner of Patents and Trademarks